(12) United States Patent
Simms

(10) Patent No.: US 6,340,350 B1
(45) Date of Patent: Jan. 22, 2002

(54) TRANSMITTER/RECEIVER STETHOSCOPE AND HOLDER THEREFOR

(76) Inventor: Juanita P. Simms, 3881 Rock Creek Rd., Rantoul, KS (US) 66079

( * ) Notice: Subject to any disclaimer, the term of this patent is extended or adjusted under 35 U.S.C. 154(b) by 0 days.

(21) Appl. No.: 09/479,460

(22) Filed: Jan. 6, 2000

(51) Int. Cl.[7] .................................................. A61B 7/04
(52) U.S. Cl. ........................................ 600/528; D3/203
(58) Field of Search ........................... 600/528; 381/67; 181/131, 132, 137; D3/203

(56) References Cited

U.S. PATENT DOCUMENTS

| | | | |
|---|---|---|---|
| 3,776,362 A | 12/1973 | Rice | |
| 4,248,241 A | 2/1981 | Tacchi | |
| 4,413,629 A | 11/1983 | Durley, III | |
| 4,705,048 A | 11/1987 | Pfohl | |
| 4,763,663 A | 8/1988 | Uphold et al. | |
| 4,777,961 A | 10/1988 | Saltzman | |
| 4,878,501 A | 11/1989 | Shue | |
| 5,027,825 A | 7/1991 | Phelps, Sr. et al. | |
| 5,035,247 A | * 7/1991 | Heimann | 600/528 |
| 5,345,509 A | 9/1994 | Hofer et al. | |
| 5,367,575 A | 11/1994 | Dieken et al. | |
| 5,467,775 A | * 11/1995 | Callahan et al. | 600/528 |
| 5,550,902 A | 8/1996 | Abbruscato | |
| 5,825,895 A | * 10/1998 | Grasfield et al. | 381/67 |

* cited by examiner

*Primary Examiner*—Jeffrey R. Jastrzab
(74) *Attorney, Agent, or Firm*—Jeffrey L. Thompson

(57) ABSTRACT

An electronic stethoscope and holder comprises a chestpiece, an earpiece, and a casing for holding the chestpiece and earpiece. The chestpiece includes a sound sensing device for sensing auscultatory sounds and converting the sounds into an electrical signal. The chestpiece further includes a radio wave transmitter for transmitting the electrical signal. The earpiece includes a receiver for receiving a transmitted electrical signal and converting the electrical signal into an audible form. The earpiece is adapted to be held in a user's ear and includes a speaker for providing an audible signal to a user. The chestpiece is particularly configured to be held comfortably between two fingers of a user's hand. A casing includes a channel recessed in a front wall and includes a pair of laterally spaced apart slots for insertion of the chestpiece therein. The casing also includes a chamber in communication with an aperture in a top wall thereof for readably holding one or more earpieces.

20 Claims, 5 Drawing Sheets

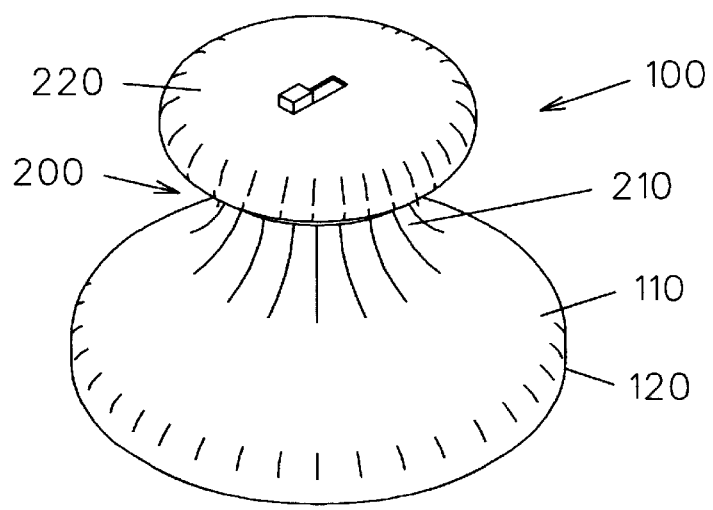
FIG. 2A
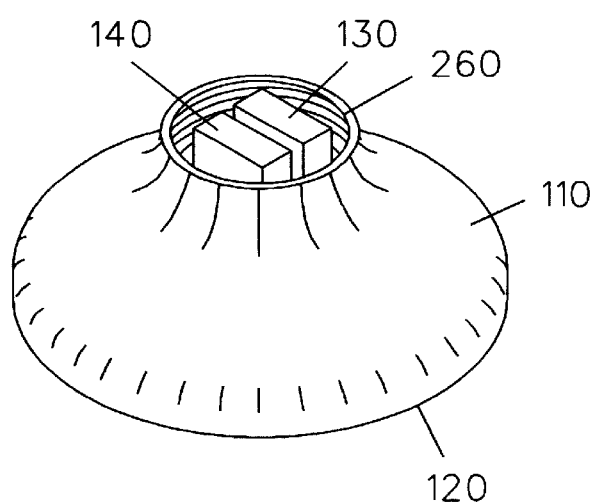
FIG. 2B
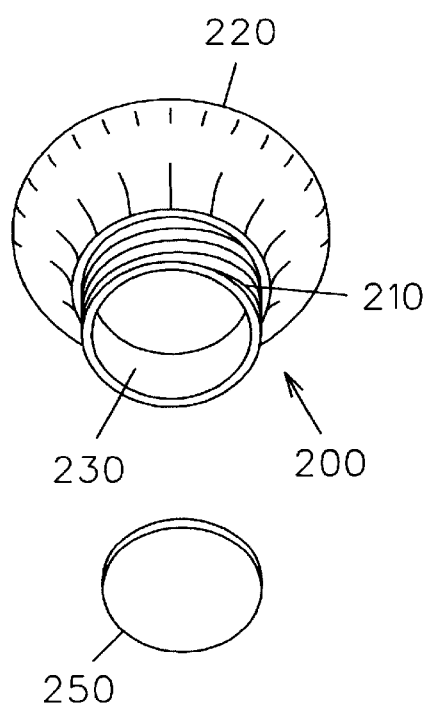

TRANSMITTER/RECEIVER STETHOSCOPE AND HOLDER THEREFOR

BACKGROUND OF THE INVENTION

This invention relates generally to stethoscopes and, more particularly, to a two-piece stethoscope having transmitter and receiver portions and a holder therefor.

The use of a stethoscope for listening to the sound of a patient's heart, lungs, or other internal organs is a routine medical practice. Therefore, doctors and nurses typically carry a stethoscope with them most of the time. A standard stethoscope, however, is inconvenient to carry in that it includes a chestpiece for placement on a patient's body, a pair of earpieces, and tubes connecting the chestpiece to the earpiece. Such a stethoscope is often carried about one's neck and dangles therefrom. A dangling chestpiece often gets in the way and interferes with other medical procedures.

Various medical devices have been proposed in the art for transmitting a signal corresponding to an auscultatory sound to a remote receiving device, such as the devices disclosed in U.S. Pat. Nos. 4,248,241, 4,705,048, and 5,027,825. Although presumably effective for their intended purposes, these devices do not provide a stethoscope that can be carried comfortably throughout the day by medical personnel and used repeatedly on different patients.

Therefore, it is desirable to have a two-piece stethoscope which includes a chestpiece for sensing and transmitting auscultatory sounds and an earpiece for receiving such sounds. It is further desirable to have a stethoscope which can be carried comfortably by medical personnel and which does not interfere with other medical procedures. In addition, it is desirable to have a stethoscope in which the chestpiece is economically configured for use by medical personnel.

SUMMARY OF THE INVENTION

A two-piece electronic stethoscope according to the present invention includes a chestpiece and an earpiece that are not connected by traditional tubes. The chestpiece includes a bell housing with a diaphragm for sensing auscultatory sounds within the chest cavity of a patient. The chestpiece also includes a transducer for converting the auscultatory sounds into an electrical signal. A transmitter coupled to the transducer transmits the electrical signal in radio wave form. The earpiece includes a housing having a configuration suitable for insertion into a user's ear. The earpiece includes a receiver for receiving a transmitted electrical signal and converting the signal into audible form. A speaker mounted within the earpiece is coupled to the receiver for providing the audible signal to the user.

The chestpiece and earpiece of the present stethoscope can be stored in a holder between uses. The holder comprises a box-like casing having a channel recessed in a front wall thereof. The channel includes a pair of slots for capturing the bell portion of the chestpiece when it is inserted into the channel. The casing also includes a chamber for holding one or more earpieces when not in use. The chamber is in communication with an aperture extending through the top wall of the casing and with an aperture at the lower end of the chamber for receiving and releasing earpieces, respectfully.

Therefore, a general object of this invention is to provide a stethoscope which includes a chestpiece for sensing and transmitting auscultatory sounds of a patient to an to earpiece insertable in a user's ear.

Another object of this invention is to provide a stethoscope, as aforesaid, in which the chestpiece is economically configured to be held and manipulated comfortably by a user.

Still another object of this invention is to provide a stethoscope, as aforesaid, in which the chestpiece and earpiece can be stored conveniently in a holder.

Yet another object of this invention is to provide a stethoscope, as aforesaid, in which the holder may be clipped to a user's belt or pocket.

A further object of this invention is to provide a stethoscope, as aforesaid, wherein no tubes connect the chestpiece with the earpiece.

Other objects and advantages of this invention will become apparent from the following description taken in connection with the accompanying drawings, wherein is set forth by way of illustration and example, embodiments of this invention.

BRIEF DESCRIPTION OF THE DRAWINGS

FIG. 2A is a perspective view of the preferred embodiment of the chestpiece of the stethoscope of FIG. 1;

FIG. 2B is an exploded view of the chestpiece of FIG. 2A;

DESCRIPTION OF THE PREFERRED EMBODIMENT

Figure 1:
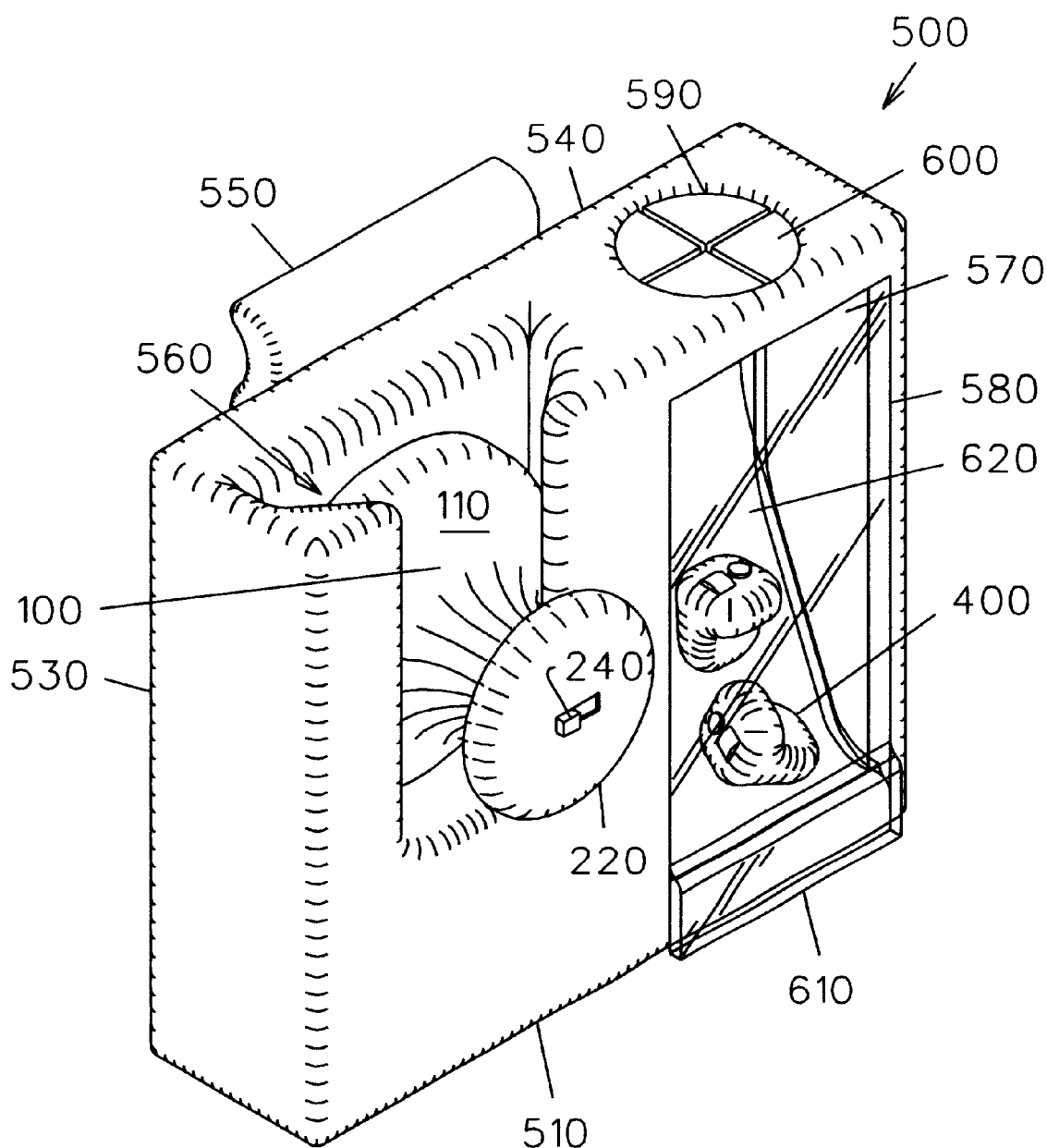
FIG. 1 is a perspective view of the stethoscope and holder therefor according to the preferred embodiment of the present invention.

A two-piece stethoscope and holder therefor according to the present invention are shown in FIG. 1. The stethoscope includes a chestpiece 100 and an earpiece 400 which are shown more particularly in FIGS. 2A through 4B. The preferred embodiment of the chestpiece 100 includes a bell housing 110 having a circular lower end covered by a metallic diaphragm for sensing auscultatory sounds within a patient's chest, such as sounds made by the heart, lungs, stomach, etc. (FIG. 2A). The bell/diaphragm configuration of the chestpiece 100, referred to generally as the sound sensing device, operates in a known manner for sensing auscultatory sounds when placed on a patient's chest or back. The bell housing 110 of the chestpiece 100 further includes a transducer 130 (FIG. 2B) which converts audible auscultatory sounds into corresponding electrical signals. The transducer 130 is coupled to a radio wave transmitter 140 which transmits the electrical signals according to a predetermined frequency. It is understand that other types of transmitters are known and would also be suitable, such as an infrared (IR) transmitter.

The chestpiece 100 also includes a handle 200 readably coupled to the bell housing 110 (FIGS. 2A and 2B). The handle 200 comprises a neck portion 210 having threads about an outer surface thereof and a top portion 220 normal to the neck portion 210. The top portion 220 extends radially outwardly from the neck portion 210 in a knob-like configuration. The neck portion 210 defines a bore 230 for receiving a battery 250 therein. Therefore, the handle 200 may be screwably coupled to the open end of the bell housing such that the transmitter 140 and transducer 130 are selectably powered by the battery 250 upon operation of an on/off switch 240 which extends through the top surface of the top portion 220. In this embodiment, the bell housing 110 includes a circular open end 260 having threads about an inner surface thereof. When the handle 200 is threadably coupled to the bell housing 110, the top portion 220 is parallel to the lower end 120 of the bell housing 110 such that two fingers of a user's hand are comfortably retained therebetween on opposing sides of the neck portion 210 during use.

Figure 3A:
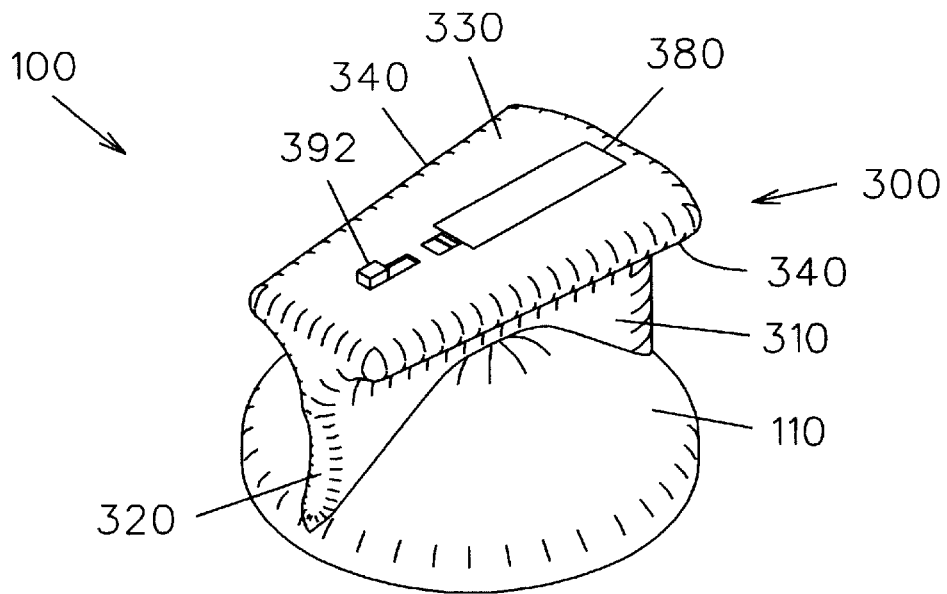
FIG. 3A is a perspective view of an alternative embodiment of the chestpiece of the stethoscope.
Figure 3B:
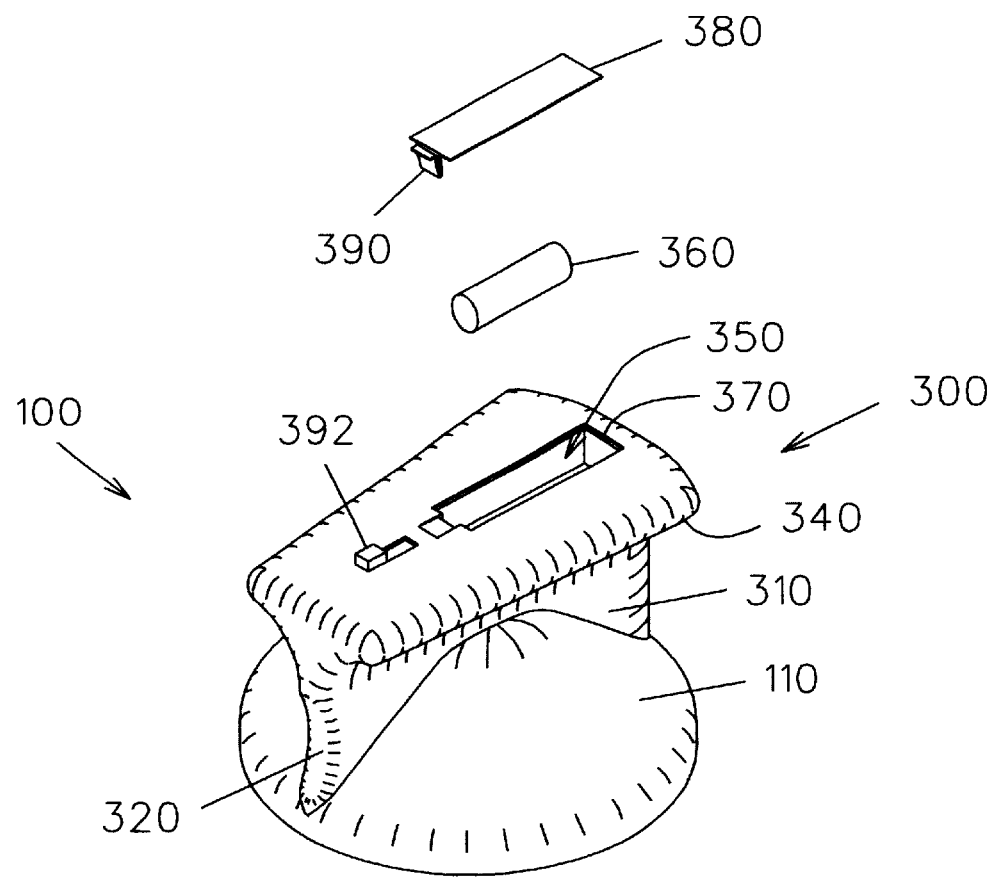
FIG. 3B is an exploded view of the chestpiece of FIG. 3A.

An alternative embodiment of the handle, denoted by reference numeral 300, may be utilized on the chestpiece 100 as shown in FIGS. 3A and 3B. A narrow neck portion 310 is fixedly attached to the bell housing 110 and extends between opposing sides of the lower end 120 thereof and also extends upwardly therefrom. One end wall 320 of the handle 300 presents a concave depression for mating with the web of a user's hand between two fingers thereof. The alternative handle 300 also includes a top portion 330 normal to the neck portion 310 and having edges 340 extending laterally away from the neck portion 310. The top portion 330 is parallel to the lower end 120 of the bell housing 110 such that two fingers of a user's hand are comfortably retained therebetween on opposing sides of the neck portion 310 during use. The handle 300 includes a compartment 350 therein for receiving a battery 360, the compartment 350 communicating with an aperture 370 extending through the top portion 330. An access door 380 is readably coupled to the top portion 330 with a spring release latch 390 or the like for selectably covering the aperture 370 (FIG. 3B). An on/off switch 392 also extends through the top portion 330 for selectably delivering current from the battery 360 to the transmitter 140 and transducer 130.

Figure 4A:
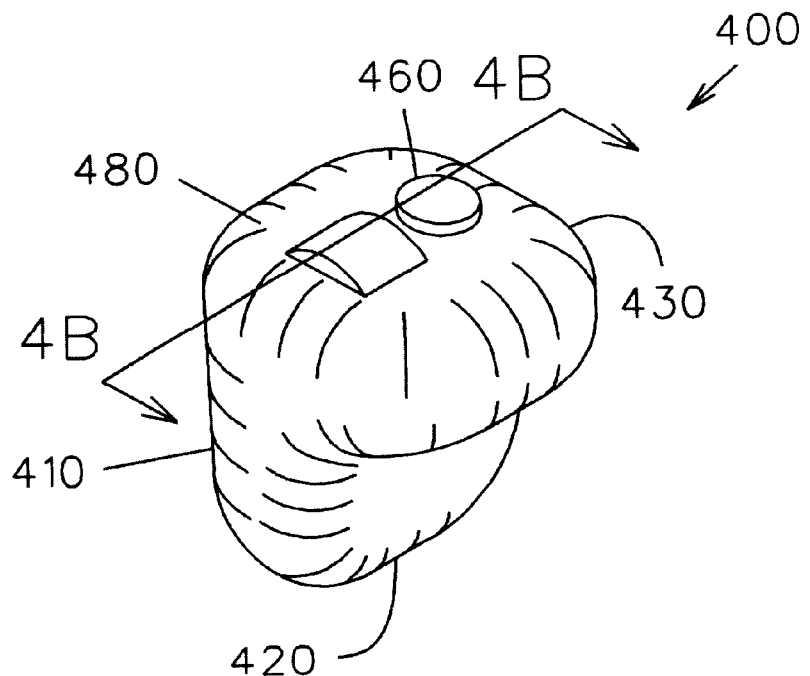
FIG. 4A is a perspective view of the earpiece of the stethoscope.
Figure 4B:
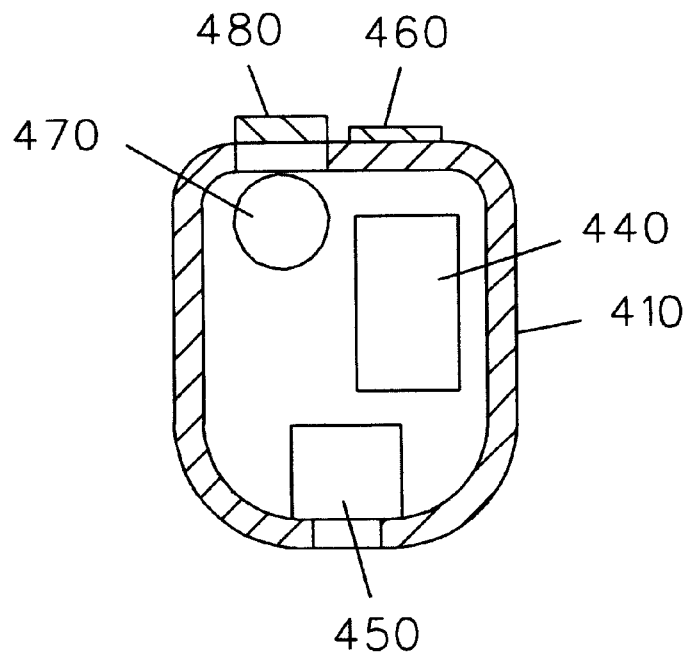
FIG. 4B is a sectional view of the earpiece taken along line 4B—4B of FIG. 4A.

As shown in FIG. 4A, the earpiece 400 includes a housing 410 having a first end 420 configured for insertion into a user's ear canal and a second end 430 configured to rest in the user's outer ear. A receiver 440 is mounted within the earpiece housing 410 for receiving and demodulating the radio wave signals transmitted by the transmitter 140. Thus, the received signals are converted again into an acoustic or audible form. It is understood that the transmitter/receiver combination according to the present invention should be constructed so as to minimize frequency interferences. This may be accomplished in part by limiting the range of transmission, i.e. only a receiver within a predetermined range will receive a transmitted signal.

A speaker 450 is mounted within the earpiece housing 410 and is operatively coupled to the receiver 440 for providing audible sounds to a user corresponding to the auscultatory sounds sensed by the sound sensing device. The speaker 450 is also coupled to a volume control knob 460 mounted on the second end 430 of the earpiece housing 410 for adjusting the volume of the speaker 450. The earpiece housing 410 further includes a battery 470 which is electrically connected to the receiver 440 and speaker 450. An access door 480 is hingedly coupled to the second end of the earpiece housing 410 for selectably replacing the battery 470.

Figure 5:
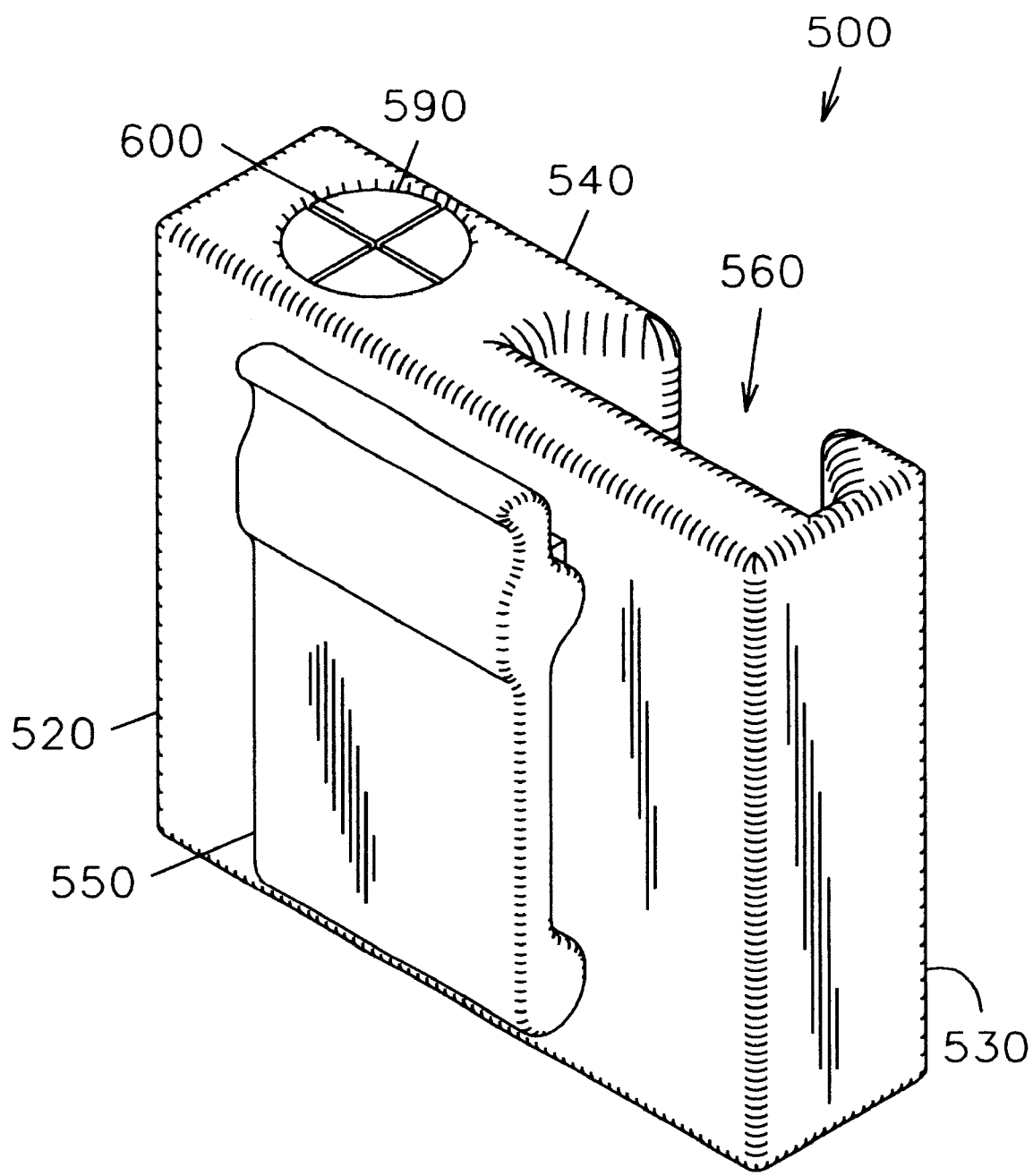
FIG. 5 is a rear perspective view of the stethoscope holder.

The present invention further includes a holder 500 for storing the chestpiece 100 and a plurality of earpieces 400 when not in use (FIGS. 1 and 5). The holder 500 comprises a box-like casing having parallel front 510 and rear 520 walls with spaced apart end walls 530 intermediate the front 510 and rear 520 walls. The casing also includes top 540 and bottom walls. A garment clasp or belt clip 550 is fixedly attached to the rear wall 520 of the casing such that the casing can be removably attached to a user's belt or garment pocket.

The casing includes a channel 560 having a dove-tail configuration recessed from the front wall 510 and including a cut-out in the front wall 510 (FIG. 1). The channel 560 includes an open top such that the bell housing 110 may be inserted therein with the neck portion 210 extending through the cut-out in the front wall 510. The dove-tail configuration retains the bell housing 110 in the channel 560. The rear wall 520 of the channel 560 may also be constructed of a magnetic material or may include a magnetic insert such that the metal diaphragm is further retained thereby.

A compartment 570 is formed between the front 510 and rear 520 walls of the casing adjacent the channel 560. The front wall 510 of the casing includes a window 580 which enables a user to see the contents of the compartment 570. The top wall 540 of the casing includes a circular aperture 590 covered by a semi-rigid perforate material 600, such as rubber or plastic, such that earpieces 400 can be inserted into the compartment 570 but cannot freely fall back out. A transparent door 610 is pivotally coupled to a lower edge of the window 580 for selectably releasing the earpieces 400 from the compartment 570. A rear wall 620 of the compartment 570 is sloped so as to guide the earpieces 400 toward the door 610.

In use, the chestpiece 100 and earpiece 400 of the stethoscope are stored in the holder 500 prior to use, as Is described above. The holder 500 may be attached to a user's clothing or belt with the clip 550. When the stethoscope is needed for a medical examination, the chestpiece 100 is slidably removed from the channel 560 and an earpiece 400 is released from the compartment 570 by pivoting the door 610 to an open position. The earpiece 400 is then inserted into the user's ear canal and the on/off switch 240 on the chestpiece 100 is placed in the "on" position. The user then slides his first and second or second and third fingers between the top portion 220 and the bell housing 110 of the chestpiece with the neck portion 210 thereof between the desired fingers. The fingers should be in a straightened position with the inner sides of the desired fingers facing one another. With the neck portion 210 bearing against the web of the user's hand between the fingers, the chestpiece 100 is placed against a patient's body for sensing auscultatory sounds.

As auscultatory sounds are sensed by the sound sensing device, the sounds are converted to electrical signals by the transducer 130 and transmitted as radio waves by the transmitter 140. The electrical signals are received by the receiver 440 in the earpiece 400 and converted back to acoustic signals. The acoustic signals are provided to a user through the speaker 450 at a volume selectable by the user. When the examination is complete, the on/off switch 240 on the chestpiece 100 is switched to the "off" position and the chestpiece 100 is slidably returned to the holder 500. The earpiece 400 is pushed through the perforate material 600 into the compartment 570.

Accordingly, the transmitter/receiver stethoscope allows medical personnel to monitor auscultatory sounds of multiple patients and then to store the stethoscope conveniently when not in use.

It is understood that while certain forms of this invention have been illustrated and described, it is not limited thereto except insofar as such limitations are included in the following claims and allowable functional equivalents thereof.

Having thus described the invention, what is claimed as new and desired to be secured by letters patent is as follows:

1. An electronic stethoscope, comprising:
    a chestpiece comprising:
        a sound sensing device for sensing auscultatory sounds and generating a signal corresponding to said sounds;
        a transmitter coupled to said sound sensing device for transmitting said signal;
        a handle coupled to said sound sensing device and configured for gripping between two fingers of a user's hand;
    an earpiece comprising:
        a receiver adapted to be inserted into a user's ear for receiving said signal and converting said signal into an audible signal; and
    a casing having a channel formed in a front wall thereof, said channel defining an open upper end adapted to retain said sound sensing device therein.

2. An electronic stethoscope as in claim 1, wherein said sound sensing device includes:
    a housing having an open end and an acoustical diaphragm covering said open end; and
    a transducer mounted in said housing for converting said auscultatory sounds into an electrical signal.

3. An electronic stethoscope as in claim 1, wherein said handle further comprises:
    a neck portion extending upwardly from said sound sensing device between opposing points along a periphery thereof, said neck portion having a narrow configuration adapted to be held between facing sides of two adjacent fingers of a user's hand;
    a planar top portion normal to said neck portion and having outwardly extending lateral edges for retaining a user's fingers between said top portion and said sound sensing device, said top portion defining said battery compartment having an open top and an access door releasably attached to said top portion for selectably covering said open top; and
    said handle defining a battery compartment adapted to receive a first battery therein for energizing said sound sensing device and said transmitter.

4. An electronic stethoscope as in claim 1, wherein said handle includes:
    a cylindrical neck portion having a plurality of threads thereabout adapted to removably mate with complementary threads on said sound sensing device, said neck portion having a bore defining said battery compartment for receiving said battery therein, said neck portion presenting a diameter smaller than a diameter of said sound sensing device adapted to be held between facing sides of two adjacent fingers of a user's hand;
    a circular top portion normal to said neck portion and having a peripheral edge extending radially outwardly from said neck portion for retaining a user's fingers between said top portion and said sound sensing device; and
    said handle defining a battery compartment adapted to receive a first battery therein for energizing said sound sensing device and said transmitter.

5. An electronic stethoscope as in claim 1, wherein said earpiece further comprises:
    an earpiece housing, said receiver and said second battery positioned within said earpiece housing;
    a speaker mounted in said earpiece housing and coupled to said receiver for providing said audible signal to a user;
    means for controlling the volume at which said speaker provides said audible signal to the user;
    an access door readably coupled to said housing for selectably providing access to said second battery; and
    a second battery electrically connected to said receiver.

6. An electronic stethoscope as in claim 1, wherein said casing includes a belt clip attached to a rear wall thereof.

7. An electronic stethoscope as in claim 1 further comprising a switch for selectively delivering a current from a first battery to said transmitter, said handle defining a battery compartment adapted to receive a first battery therein for energizing said sound sensing device and said transmitter.

8. An electronic stethoscope, comprising:
    a chestpiece comprising:
        a housing having an open end and an acoustical diaphragm covering said open end for detecting sound waves from a body portion of a patient;
        a transducer mounted in said housing for converting said sound waves into electrical signals;
        a radio wave transmitter mounted in said housing and coupled to said transducer for transforming said electrical signals into radio wave signals and transmitting said radio wave signals;
        a handle coupled to said housing and configured for gripping between two fingers of a user's hand, said handle defining a battery compartment adapted to receive a first battery therein, said first battery being electrically connected to said transducer and said transmitter;
    an earpiece comprising:
        an earpiece housing;
        a receiver mounted in said earpiece housing for receiving said radio wave signals and converting said radio wave signals to audio signals;
        a speaker mounted in said earpiece housing and operatively connected to said receiver for providing said audio signals to a user; and
        a second battery positioned in said earpiece housing and electrically connected to said receiver and said speaker; and
    a casing having a channel formed in a front wall thereof, said channel having a dove-tail configuration with an open upper end adapted to retain said sound sensing device therein.

9. An electronic stethoscope as in claim 8, wherein said handle further comprises:
    a neck portion extending upwardly from said housing between opposing points along a periphery thereof, said neck portion having a narrow configuration adapted to be held between facing sides of two adjacent fingers of a user's hand; and
    a planar top portion normal to said neck portion and having outwardly extending lateral edges for retaining a user's fingers between said top portion and said housing, said top portion defining said battery compartment having an open top and an access door releasably attached to said top portion for selectably covering said open top.

10. An electronic stethoscope as in claim 8, wherein said handle includes:
    a cylindrical neck portion having a plurality of threads thereabout adapted to removably mate with complementary threads on said housing, said neck portion having a bore defining said battery compartment for receiving said battery therein, said neck portion presenting a diameter smaller than a diameter of said housing adapted to be held between facing sides of two adjacent fingers of a user's hand; and a circular top portion normal to said neck portion and having a peripheral edge extending radially outwardly from said neck portion for retaining a user's fingers between said top portion and said sound sensing device.

11. An electronic stethoscope as in claim 8 wherein said earpiece includes means for controlling the volume of said speaker, said earpiece housing including a door readably coupled thereto for providing access to said second battery.

12. An electronic stethoscope as in claim 8, wherein said casing includes a belt clip attached to a rear wall thereof.

13. An electronic stethoscope as in claim 8 further comprising a switch for selectively delivering a current from said first battery to said transmitter.

14. In combination, an electronic stethoscope and holder therefor, comprising:

a chestpiece comprising:
a sound sensing device having a metallic diaphragm for sensing auscultatory sounds and generating an electrical signal corresponding to said sounds;
a radio wave transmitter coupled to said sound sensing device for transforming said electrical signal into a radio wave signal and transmitting said radio wave signal;
a handle coupled to said sound sensing device and configured for selectably receiving two fingers of a user's hand, said handle defining a compartment adapted for receiving a first battery therein, said battery being electrically connected to said sound sensing device and said transmitter;

an earpiece comprising:
a receiver adapted to be inserted into a user's ear for receiving said radio wave signal and converting said radio wave signal into audible form;
a second battery electrically connected to said receiver; and a box-like casing comprising:
a front wall forming a channel, said channel having a dove-tail configuration and an open upper end such that said sound sensing device is retained in said channel and said handle extends through said channel.

15. An electronic stethoscope and holder therefor as in claim 14, wherein said handle further comprises:

a neck portion extending upwardly from said sound sensing device between opposing points along a periphery thereof, said neck portion having a narrow configuration adapted to be held between facing sides of two adjacent fingers of a user's hand; and a planar top portion normal to said neck portion and having outwardly extending lateral edges for retaining a user's fingers between said top portion and said sound sensing device, said top portion defining said battery compartment having an open top and an access door releasably attached to said top portion for selectably covering said open top.

16. An electronic stethoscope and holder therefor as in claim 14, wherein said handle includes:

a cylindrical neck portion having a plurality of threads thereabout adapted to removably mate with complementary threads on said sound sensing device, said neck portion having a bore defining said battery compartment for receiving said battery therein, said neck portion presenting a diameter smaller than a diameter of said sound sensing device adapted to be held between facing sides of two adjacent fingers of a user's hand; and a circular top portion normal to said neck portion and having a peripheral edge extending radially outwardly from said neck portion for retaining a user's fingers between said top portion and said sound sensing device.

17. An electronic stethoscope and holder therefor as in claim 14, wherein said channel includes a magnetic surface recessed into said front wall of said casing such that said metallic diaphragm of said sound sensing device is magnetically retained against said magnetic surface.

18. An electronic stethoscope and holder therefor as in claim 14, wherein said casing further includes:

a top wall defining an aperture therein, said aperture covered by a semi-rigid perforated material;
a chamber in communication with said aperture such that said earpiece is receivable into said chamber through said aperture, said perforated material inhibiting release of said earpiece from said chamber through said aperture; and
a door pivotally coupled to said chamber for selectably releasing said earpiece from said chamber.

19. An electronic stethoscope and holder therefor as in claim 14, wherein said casing includes a belt clip attached to a rear wall thereof.

20. An electronic stethoscope and holder therefor as in claim 14, further comprising an on/off switch for selectably delivering current from said first battery to said sound sensing device and said transmitter.

* * * * *